US00PP21098P2

(12) United States Plant Patent
Giesen

(10) Patent No.: US PP21,098 P2
(45) Date of Patent: Jun. 22, 2010

(54) ***SUTERA* PLANT NAMED 'CAY JULAV'**
(50) Latin Name: *Sutera cordata*
Varietal Denomination: Cay Julav

(75) Inventor: Eric Giesen, Andijk (NL)

(73) Assignee: Goldsmith Seeds Europe B.V., Andijk (NL)

( * ) Notice: Subject to any disclaimer, the term of this patent is extended or adjusted under 35 U.S.C. 154(b) by 0 days.

(21) Appl. No.: 12/384,121

(22) Filed: Apr. 1, 2009

(51) Int. Cl.
*A01H 5/00* (2006.01)

(52) U.S. Cl. ..... Plt./485
(58) Field of Classification Search ..... Plt./485
See application file for complete search history.

*Primary Examiner*—Kent L Bell
(74) *Attorney, Agent, or Firm*—S. Matthew Edwards

(57) ABSTRACT

A new *Sutera* plant named 'Cay Julav' particularly distinguished by large flowers of uniform, lavender color, deep green foliage, cordate, relatively small leaves, well branching and moderately tight, low mounding and trailing plant habit of about medium size.

1 Drawing Sheet

Latin name of the genus and species of the plant claimed: *Sutera cordata.*

Varietal denomination: 'Cay Julav'.

BACKGROUND OF THE NEW PLANT

The present invention comprises a new and distinct cultivar of *Sutera*, botanically known as *Sutera cordata* and hereinafter referred to by the cultivar name 'Cay Julav'.

'Cay Julav' is a product of a planned breeding program. The new cultivar originated from a hybridization made in Andijk, Netherlands, in July 2005.

The female parent was an unpatented, proprietary *Sutera* plant designated 'BA04-142-1', having somewhat larger flowers and lighter lavender flower color, as well as shorter stems than 'Cay Julav'.

The male parent of 'Cay Julav' was an unpatented proprietary *Sutera* plant designated 'BA04-8-1', having purple flower color, less deep green foliage and smaller plant size than 'Cay Julav'.

The resulting seeds were sown in October 2005, and 'Cay Julav' was selected as one flowering plant within the progeny of the stated cross in January 2006 in a controlled environment in Andijk, Netherlands.

The first act of asexual reproduction of 'Cay Julav' was accomplished when vegetative cuttings were used from the initial selection in the spring of 2006 in a controlled environment in Andijk, Netherlands.

Horticultural examination of plants grown from cuttings of the plant initiated in the spring of 2006 in Andijk, The Netherlands, and continuing thereafter, has demonstrated that the combination of characteristics as herein disclosed for 'Cay Julav' are firmly fixed and are retained through successive generations of asexual reproduction.

'Cay Julav' has not been observed under all possible environmental conditions. The phenotype may vary significantly with variations in environment such as temperature, light intensity and day length.

Plant Breeders' Rights for this cultivar was applied for with the European Union (CPVO) on Jul. 21, 2008. 'Cay Julav' has not been made publicly available more than one year prior to the filing of this application.

DESCRIPTION OF DRAWINGS

This new *Sutera* plant is illustrated by the accompanying photograph which shows blooms, buds, and foliage of the plant in full color. The colors shown are as true as can be reasonably obtained by conventional photographic procedures. The photograph shows a close-up view of the shoot tips with buds and flowers, and the inset shows a single flower.

DETAILED BOTANICAL DESCRIPTION

The measurements were taken in Hillscheid, Germany, on mid June 2008 on 17–18 week old plants that were growing (3 each) in 25 cm diameter baskets in a greenhouse at relatively cool conditions. Culture of these plants had started in early February 2008 with planting of rooted cuttings that had been pinched once.

Color chart used: The Royal Horticultural Society Colour Chart (R.H.S.), 2001.

BRIEF SUMMARY OF THE INVENTION

The following observations, measurements, and comparisons describe plants grown indoors and outdoors in Andijk, Netherlands, and in Hillscheid, Germany. The following traits have been repeatedly observed and are determined to be basic characteristics of the new variety. The combination of these characteristics distinguishes this *Sutera* as a new and distinct variety:

1. Large, lavender colored flowers
2. Deep green foliage, relatively small, cordate leaves.
3. Well branched, moderately tight plant habit.
4. Initially mounding, later overhanging and trailing habit of about medium size.

COMPARISON WITH COMMERCIAL CULTIVARS

'Cay Julav' differs from the commercial cultivar 'Taifun Blue', patented as 'Wesbavio', U.S. Plant Pat. No. 14,481, in that 'Cay Julav' has larger flowers, lighter lavender flower color and fewer, but thicker stems than 'Taifun Blue'.

'Cay Julav' differs from the commercial cultivar 'Gulliver Blue Impr.' (Synonym 'Glacier Blue Improved'), protected 'Danova900', U.S. Plant Pat. No. 17,896, in that 'Cay Julav' has a lighter lavender hue of flower color, thicker stems and larger leaves.

Plant:

*Growth and habit.*—Medium vigor, bushy, well-branched habit; medium to strong branching in combination with a medium length of internodes results in a bushy, but not extremely tight plant structure; initially upright and mounding, later trailing habit.

*Height.*—About 15 cm (above soil).

*Width* (*diameter including flowers*).—30–40 cm, including flowers.

*Spread* (*including flowers*).—Approximately 60–65, for the whole basket as shown in the photograph.

*Number of branches.*—About 20–25.

*Time to produce a finished flowering plant,*—About 12 weeks for a 12 cm pot.

*Outdoor plant performance.*—Used for hanging baskets or in mixed container plantings.

*Time to initiate and develop roots.*—21 days at 20–24° C.

*Root description.*—Fine, fibrous and freely branching.

Stem:

*Characteristics.*—Cross section round, intermediate degree of self-branching.

*Stem length.*—25–35 cm.

*Diameter.*—2–3 mm at mid portion.

*Internode length.*—1.5–2.5 cm.

*Color.*—RHS 144B, no anthocyanin.

*Texture.*—Dense pubescence.

Foliage:

*Arrangement.*—Opposite.

*Leaf shape.*—Broad, ovate to elliptical.

*Apex.*—Acute to obtuse.

*Base.*—Obtuse to attenuate.

*Margin.*—Dentate.

*Leaf length.*—Up to 1.2 cm.

*Leaf width.*—Up to 1.0 cm.

*Immature leaf, color upper surface.*—RHS 137D to 143A.

*Immature leaf, color lower surface.*—RHS 138A to 143B.

*Mature color upper surface.*—RHS 137A.

*Mature color lower surface.*—RHS 137B.

*Venation type.*—Weakly pinnate.

*Venation color of lower surface.*—RHS 143C.

*Texture.*—Both surfaces covered with short pubescence.

Inflorescence:

*Blooming habit.*—Continuous through the growing season from spring to the fall.

*Quantity of inflorescences per stem.*—About 2–4 open flowers and additional buds.

*Type of inflorescence.*—Flowers are solitary, most often 2 flowers per node are developed.

*Fragrance.*—Absent.

Peduncle:

*Color.*—RHS 143B or 143C.

*Length.*—About 0.5 cm.

*Diameter.*—1 mm.

*Texture.*—Pubescent.

Flower:

*Corolla type and shape.*—Single-type, nearly round, lower part tube and funnel shaped formed by 5 fused petals, upper part is salver shaped formed by the partly free petal lobes.

*Flower, horizontal diameter.*—1.8–2.1 cm.

*Flower, total length.*—1.1–1.2 cm.

*Flower tube diameter.*—3–4 mm.

*Color upper surface.*—RHS N88C, uniform.

*Color lower surface: RHS N*88D or slightly lighter.

*Color of the throat, inside.*—RHS 21A.

*Color of the tube, outside.*—RHS 20A.

*Texture of tube.*—Pubescent.

Petal (lobes):

*Apex.*—Rounded.

*Base.*—Fused.

*Margin.*—Entire.

*Texture.*—Glabrous.

Flower bud:

*Shape.*—Obovate or cone-shaped.

*Diameter.*—About 0.4–0.5 cm.

*Length.*—About 1.2 cm.

*Color* (*at tight bud*).—RHS N88C.

Calyx:

*Shape.*—Whorl of 5 sepals surrounding the base of the flower tube, sepals are fused at the base and lanceolate in shape.

*Sepal color.*—RHS 143A.

*Length.*—0.1 cm.

*Width.*—0.5 cm.

*Apex.*—Acute.

*Base.*—Fused.

*Texture.*—Covered with dense pubescence.

Pedicel:

*Color.*—RHS 137C.

*Length.*—0.4–1.0 cm.

*Diameter.*—0.1 cm.

*Texture.*—Short, dense pubescence.

Reproductive organs:

Stamens:

*Quantity.*—4.

*Filament, color.*—White, RHS 155A, lower end RHS 150D.

*Length.*—1.3–1.5 cm.

*Diameter.*—0.1 cm.

*Anther color.*—RHS 12B.

*Pollen amount.*—Moderate.

*Pollen color.*—Yellow, RHS 12A.

Pistil:

*Quantity per flower.*—One.

*Length.*—1.5 cm.

*Stigma color.*—RHS 145B.

*Style color.*—RHS 145C.

Fruit and seed set: Has not been observed.

Disease and insect resistance: Resistance and susceptibility typical for the species, no special observations made.

What is claimed is:

1. A new and distinct cultivar of *Sutera* plant named 'Cay Julav' substantially as illustrated and described herein.

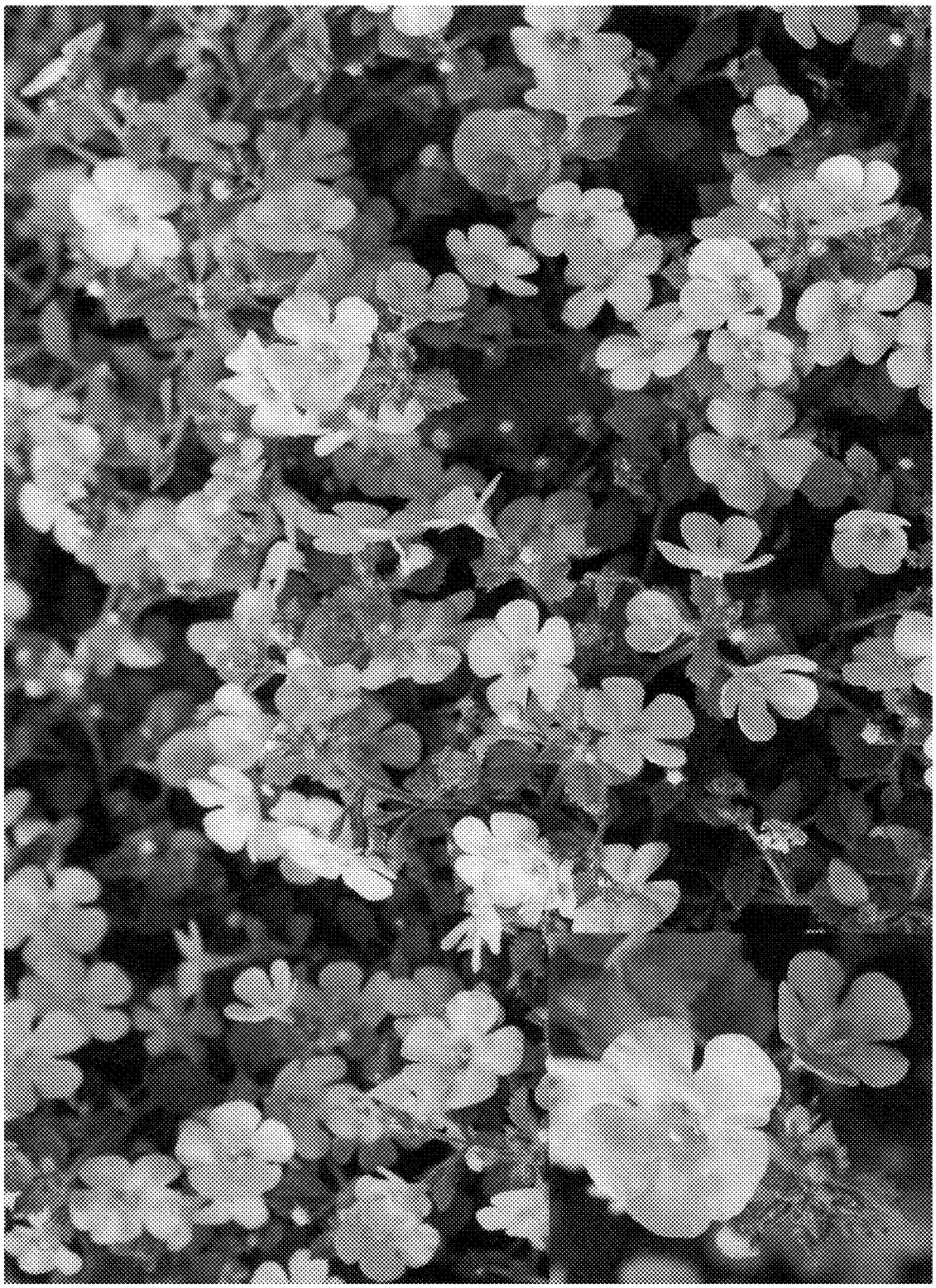

* * * * *